(12) United States Patent
Ramezanzadeh Moghadam et al.

(10) Patent No.: US 12,303,716 B2
(45) Date of Patent: May 20, 2025

(54) METHODS FOR RADIATION DELIVERY QUALITY ASSURANCE

(71) Applicant: RefleXion Medical, Inc., Hayward, CA (US)

(72) Inventors: Amir Ramezanzadeh Moghadam, San Jose, CA (US); George Andrew Zdasiuk, Portola Valley, CA (US)

(73) Assignee: RefleXion Medical, Inc., Hayward, CA (US)

( * ) Notice: Subject to any disclaimer, the term of this patent is extended or adjusted under 35 U.S.C. 154(b) by 355 days.

(21) Appl. No.: 18/146,321

(22) Filed: Dec. 23, 2022

(65) Prior Publication Data

US 2023/0201629 A1 Jun. 29, 2023

Related U.S. Application Data

(60) Provisional application No. 63/294,047, filed on Dec. 27, 2021.

(51) Int. Cl.
*A61N 5/10* (2006.01)

(52) U.S. Cl.
CPC .......... *A61N 5/1042* (2013.01); *A61N 5/1045* (2013.01)

(58) Field of Classification Search
CPC .. A61N 5/1042; A61N 5/1045; A61N 5/1071; A61N 2005/1076; A61N 2005/1091
See application file for complete search history.

(56) References Cited

U.S. PATENT DOCUMENTS

| | | | |
|---|---|---|---|
| 3,418,475 A | 12/1968 | Hudgens | |
| 3,668,399 A | 6/1972 | Cahill et al. | |
| 3,721,826 A | 3/1973 | Thomas, Jr. | |
| 3,779,135 A | 12/1973 | Sugimura | |
| 3,936,647 A | 2/1976 | Fekete | |
| 4,086,494 A | 4/1978 | Malak | |
| 4,241,644 A | 12/1980 | Schertler | |
| 4,246,488 A | 1/1981 | Hura | |
| 4,361,902 A | 11/1982 | Brandt et al. | |
| 4,527,769 A | 7/1985 | Stogner et al. | |
| 4,628,499 A | 12/1986 | Hammett | |
| 4,760,589 A | 7/1988 | Siczek | |
| 4,794,629 A | 12/1988 | Pastyr et al. | |
| 5,010,312 A | 4/1991 | Motykiewicz | |
| 5,317,616 A | 5/1994 | Swerdloff et al. | |

(Continued)

FOREIGN PATENT DOCUMENTS

| | | |
|---|---|---|
| CN | 2529663 Y | 1/2003 |
| CN | 1799509 A | 7/2006 |

(Continued)

OTHER PUBLICATIONS

Extended European Search Report mailed on Mar. 18, 2019, for European Patent Application No. 16 808 458.0, filed on Jun. 10, 2016, 8 pages.

(Continued)

*Primary Examiner* — Courtney D Thomas
(74) *Attorney, Agent, or Firm* — Cooley LLP

(57) ABSTRACT

Described herein are methods and systems for generating a MV detector image for evaluating the quality of radiation delivery according to a radiotherapy treatment plan. The MV detector image is generated from MV detector measurements of a small number of multi-leaf collimator (MLC) leaf openings.

51 Claims, 7 Drawing Sheets

(56) References Cited

U.S. PATENT DOCUMENTS

| | | |
|---|---|---|
| 5,351,280 A | 9/1994 | Swerdloff et al. |
| 5,394,452 A | 2/1995 | Swerdloff et al. |
| 5,408,591 A | 4/1995 | Shih et al. |
| 5,495,376 A | 2/1996 | Wasson et al. |
| 5,596,619 A | 1/1997 | Carol |
| 5,757,881 A | 5/1998 | Hughes |
| 6,052,436 A | 4/2000 | Huttner et al. |
| 6,137,114 A | 10/2000 | Rohe et al. |
| 6,449,340 B1 | 9/2002 | Tybinkowski et al. |
| 6,895,751 B1 | 5/2005 | Greentree |
| 7,519,162 B2 | 4/2009 | Hoffmann |
| 7,783,007 B2 | 8/2010 | Echner |
| 8,017,915 B2 | 9/2011 | Mazin |
| 8,107,589 B2 | 1/2012 | Sakurai et al. |
| 8,605,857 B1 | 12/2013 | Renner |
| 9,019,307 B1 | 4/2015 | Grimm |
| 9,443,633 B2 | 9/2016 | Orton et al. |
| 10,456,600 B2 | 10/2019 | Owens et al. |
| 10,500,416 B2 | 12/2019 | Larkin et al. |
| 10,695,586 B2 | 6/2020 | Harper et al. |
| 10,702,715 B2 | 7/2020 | Pearce et al. |
| 11,285,340 B2 | 3/2022 | Larkin et al. |
| 2004/0030246 A1 | 2/2004 | Townsend et al. |
| 2004/0079899 A1 | 4/2004 | Ma |
| 2004/0122308 A1 | 6/2004 | Ding |
| 2005/0063516 A1 | 3/2005 | Kato et al. |
| 2005/0197564 A1 | 9/2005 | Dempsey |
| 2006/0113482 A1 | 6/2006 | Pelizzari et al. |
| 2006/0173294 A1 | 8/2006 | Ein-Gal |
| 2006/0193441 A1 | 8/2006 | Cadman |
| 2006/0272494 A1 | 12/2006 | Cetinkunt et al. |
| 2007/0164239 A1 | 7/2007 | Terwilliger et al. |
| 2007/0251379 A1 | 11/2007 | Lund |
| 2008/0035870 A1 | 2/2008 | Wygnanski et al. |
| 2008/0165930 A1 | 7/2008 | Perkins |
| 2009/0200476 A1 | 8/2009 | Brusasco et al. |
| 2009/0256078 A1 | 10/2009 | Mazin |
| 2010/0040197 A1 | 2/2010 | Maniawski et al. |
| 2010/0054408 A1 | 3/2010 | Echner |
| 2011/0049377 A1 | 3/2011 | Morf et al. |
| 2011/0200170 A1 | 8/2011 | Nord et al. |
| 2011/0210261 A1 | 9/2011 | Maurer, Jr. |
| 2012/0035470 A1 | 2/2012 | Kuduvalli et al. |
| 2012/0203490 A1 | 8/2012 | Sayeh et al. |
| 2012/0213334 A1 | 8/2012 | Dirauf et al. |
| 2012/0234023 A1 | 9/2012 | Mizuno |
| 2012/0250971 A1 | 10/2012 | Holmes et al. |
| 2012/0317994 A1 | 12/2012 | Matsubara |
| 2013/0251109 A1 | 9/2013 | Becca et al. |
| 2014/0079179 A1 | 3/2014 | Takagaki et al. |
| 2014/0239204 A1 | 8/2014 | Orton et al. |
| 2014/0270053 A1 | 9/2014 | Larson |
| 2015/0126801 A1 | 5/2015 | Matteo et al. |
| 2015/0150740 A1 | 6/2015 | Lewald et al. |
| 2015/0170778 A1 | 6/2015 | Echner et al. |
| 2015/0190658 A1 | 7/2015 | Yu |
| 2015/0224342 A1 | 8/2015 | Baltes et al. |
| 2015/0283403 A1 | 10/2015 | Kapatoes et al. |
| 2015/0360056 A1 | 12/2015 | Xing et al. |
| 2016/0140300 A1 | 5/2016 | Purdie et al. |
| 2016/0193480 A1 | 7/2016 | Ribbing et al. |
| 2016/0361566 A1 | 12/2016 | Larkin et al. |
| 2016/0361568 A1 | 12/2016 | Chappelow et al. |
| 2017/0095678 A1 | 4/2017 | Oster et al. |
| 2018/0185672 A1 | 7/2018 | Ramezanzadeh Moghadam |
| 2018/0345042 A1 | 12/2018 | Voronenko et al. |
| 2018/0369611 A1 | 12/2018 | Owens et al. |
| 2019/0054320 A1 | 2/2019 | Owens et al. |
| 2020/0197729 A1 | 6/2020 | Owens et al. |
| 2020/0368557 A1 | 11/2020 | Harper et al. |
| 2021/0011178 A1 | 1/2021 | Kapatoes |
| 2022/0001209 A1 | 1/2022 | Owens et al. |
| 2022/0193451 A1 | 6/2022 | Duval et al. |

FOREIGN PATENT DOCUMENTS

| | | |
|---|---|---|
| CN | 101267767 A | 9/2008 |
| CN | 101297759 A | 11/2008 |
| CN | 101378805 A | 3/2009 |
| CN | 101908348 A | 12/2010 |
| CN | 102467985 A | 5/2012 |
| CN | 102755696 A | 10/2012 |
| CN | 102760505 A | 10/2012 |
| CN | 202620505 U | 12/2012 |
| CN | 103071241 A | 5/2013 |
| CN | 103209736 A | 7/2013 |
| CN | 103650095 A | 3/2014 |
| CN | 104519958 A | 4/2015 |
| DE | 10-2013-205606 A1 | 10/2014 |
| EP | 0 437 434 A1 | 7/1995 |
| EP | 0 817 978 A1 | 8/2001 |
| EP | 1 762 177 A2 | 3/2007 |
| EP | 2 072 081 A1 | 6/2009 |
| EP | 2 708 919 A2 | 3/2014 |
| EP | 2 904 974 A1 | 8/2015 |
| EP | 2 872 913 B1 | 2/2016 |
| EP | 2 990 078 A1 | 3/2016 |
| FR | 2839894 A1 | 11/2003 |
| GB | 2341301 A | 3/2000 |
| GB | 69634119 T2 | 2/2006 |
| GB | 2513596 A | 11/2014 |
| JP | H-01-156830 A | 6/1989 |
| JP | H-08-511451 A | 12/1996 |
| JP | H-09-122110 A | 5/1997 |
| JP | 2002-263090 A | 9/2002 |
| JP | 03-277350 A | 10/2003 |
| JP | 2008-173184 A | 7/2008 |
| JP | 2009-160308 A | 7/2009 |
| JP | 2009-538195 A | 11/2009 |
| JP | 2010-500910 A | 1/2010 |
| JP | 2013-059576 A | 4/2013 |
| JP | 2013-545560 A | 12/2013 |
| JP | 2014-503315 A | 2/2014 |
| JP | 2014-521370 A | 8/2014 |
| JP | 2016-055161 A | 4/2016 |
| NL | 9520013 A | 2/1997 |
| WO | WO-00/59576 A1 | 10/2000 |
| WO | WO-2010/109585 A1 | 9/2010 |
| WO | WO-2012/135771 A1 | 10/2012 |
| WO | WO-2013/024380 A1 | 2/2013 |
| WO | WO-2015/038832 A1 | 3/2015 |
| WO | WO-2015/103564 A1 | 7/2015 |
| WO | WO-2015/134953 A1 | 9/2015 |
| WO | WO-2015/161036 A1 | 10/2015 |
| WO | WO-2016/172352 A1 | 10/2016 |
| WO | WO-2017/081768 A1 | 5/2017 |
| WO | WO-2018/183748 A1 | 10/2018 |
| WO | WO-2020/144134 A1 | 7/2020 |
| WO | WO-2021/011207 A1 | 1/2021 |
| WO | WO-2022/036707 A1 | 2/2022 |
| WO | WO-2022/144538 A1 | 7/2022 |
| WO | WO-2022/182681 | 9/2022 |

OTHER PUBLICATIONS

Extended European Search Report mailed on Jun. 9, 2020, for EP Application No. 17 871 349.1, filed on Nov. 15, 2017, 6 pages.

Extended European Search Report mailed on Mar. 15, 2021, for EP Application No. 18 837 615.6, filed on Jul. 26, 2018, 8 pages.

Extended European Search Report mailed on Mar. 30, 2022, for EP Application No. 21 195 331.0, filed on Nov. 15, 2017, 11 pages.

Fan, Q. et al. (2012). "Emission Guided Radiation Therapy for Lung and Prostrate Cancers: A Feasibility Study on a Digital Patient," *Med. Phys.* 39(11):7140-7152.

Fan, Q. et al. (2013). "Toward a Planning Scheme for Emission Guided Radiation Therapy (EGRT): FDG Based Tumor Tracking in a Metastatic Breast Cancer Patient," *Med. Phys.* 40(8): 12 pages.

Final Office Action mailed on Nov. 1, 2018, for U.S. Appl. No. 15/179,823, filed Jun. 10, 2016, 12 pages.

Final Office Action mailed on Jul. 14, 2021, for U.S. Appl. No. 16/582,308, filed Sep. 25, 2019, 8 pages.

(56) References Cited

OTHER PUBLICATIONS

Final Office Action mailed on Sep. 15, 2022, for U.S. Appl. No. 16/582,308, filed Sep. 25, 2019, 10 pages.
Internal Atomic Energy Agency (Oct. 2008). "The Role of PET/CT in Radiation Treatment Planning for Cancer Patient Treatment," located at https://www-pub.iaea.org/MTCD/Publications/PDF/te_1603_web.pdf, 40 total pages.
International Search Report mailed on Sep. 16, 2016, for PCT Application No. PCT/US2016/037051, filed on Jun. 10, 2016, 3 pages.
International Search Report mailed on Mar. 7, 2018, for PCT Application No. PCT/US2017/061848, filed on Nov. 15, 2017, 4 pages.
International Search Report mailed on Oct. 3, 2018, for PCT Application No. PCT/US2018/043954, filed on Jul. 26, 2018, 3 pages.
International Search Report mailed on Aug. 24, 2022, for PCT Application No. PCT/US2022/017375, filed on Feb. 22, 2022, 7 pages.
International Search Report mailed on Feb. 23, 2023, for PCT Application No. PCT/US2022/079175, filed on Nov. 2, 2022, 6 pages.
Islam, M.K. (2009). "An integral quality monitoring system for real-time verification of intensity modulated radiation therapy," Med. Phys. 36:5420-5428.
Merriam-Webster Dictionary (2018). "Couple," located at https://web.archive.org/web/20150403230112/https://www.merriam-webster.com/dictionary/couple.
Muller, L. (May 2018). "Maritimes an der waterkant," Neus von Dolphin & Compass, Presentation, 53 total pages.
Non-Final Office Action mailed on Aug. 30, 2018, for U.S. Appl. No. 15/179,823, filed Jun. 10, 2016, 11 pages.
Non-Final Office Action mailed on Mar. 8, 2019, for U.S. Appl. No. 15/179,823, filed Jun. 10, 2016, 11 pages.
Non-Final Office Action mailed on Jan. 7, 2020, for U.S. Appl. No. 15/814,222, filed Nov. 15, 2017, 13 pages.
Non-Final Office Action mailed on Feb. 11, 2021, for U.S. Appl. No. 16/582,308, filed Sep. 25, 2019, 9 pages.
Non-Final Office Action mailed on May 5, 2021, for U.S. Appl. No. 16/677,200, filed Nov. 7, 2019, 15 pages.
Non-Final Office Action mailed on Jun. 8, 2022, for U.S. Appl. No. 16/582,308, filed Sep. 25, 2019, 9 pages.
Non-Final Office Action mailed on Dec. 14, 2022, for U.S. Appl. No. 16/887,852, filed May 29, 2020, 12 pages.
Notice of Allowance mailed on Jul. 25, 2019, for U.S. Appl. No. 16/046,746, filed Jul. 26, 2018, 8 pages.
Notice of Allowance mailed on Aug. 15, 2019, for U.S. Appl. No. 16/046,746, filed Jul. 26, 2018, 7 pages.
Notice of Allowance mailed on Sep. 23, 2019, for U.S. Appl. No. 15/179,823, filed Jun. 10, 2016, 10 pages.
Notice of Allowance mailed on Apr. 30, 2020, for U.S. Appl. No. 15/814,222, filed Nov. 15, 2017, 10 pages.
Notice of Allowance mailed on Oct. 28, 2021, for U.S. Appl. No. 16/677,200, filed Nov. 7, 2019, 11 pages.
Shirvani, S.M. et al. (Jan. 2021). "Biology-guided radiotherapy: redefining the role of radiotherapy in metastatic cancer," Br. J. Radiol. 94:20200873, 10 total pages.
Thorwarth, D. et al. (2010). "Physical radiotherapy treatment planning based on functional PET/CT data," Radiotherapy Oncology, pp. 317-324.
Written Opinion of the International Searching Authority mailed on Sep. 16, 2016, for PCT Application No. PCT/US2016/037051, filed on Jun. 10, 2016, 5 pages.
Written Opinion of the International Searching Authority mailed on Mar. 7, 2018, for PCT Application No. PCT/US2017/061848, filed on Nov. 15, 2017, 5 pages.
Written Opinion of the International Searching Authority mailed on Oct. 3, 2018, for PCT Application No. PCT/US2018/043954, filed on Jul. 26, 2018, 5 pages.
Written Opinion of the International Searching Authority mailed on Aug. 24, 2022, for PCT Application No. PCT/US2022/017375, filed on Feb. 22, 2022, 11 pages.
Written Opinion of the International Searching Authority mailed on Feb. 23, 2023, for PCT Application No. PCT/US2022/079175, filed on Nov. 2, 2022, 9 pages.
Corrected Notice of Allowability mailed on Jan. 30, 2024, for U.S. Appl. No. 16/887,852, filed May 29, 2020, 2 pages.
Final Office Action mailed on Oct. 4, 2023, for U.S. Appl. No. 17/479,873, filed Sep. 20, 2021, 10 pages.
Final Office Action mailed on Jul. 8, 2024, for U.S. Appl. No. 17/479,873, filed Sep. 20, 2021, 11 pages.
International Search Report mailed on May 9, 2023, for PCT Application No. PCT/US2022/082375, filed on Dec. 23, 2022, 4 pages.
International Search Report mailed on Jun. 6, 2024, for PCT Application No. PCT/US2023/085347, filed on Dec. 21, 2023, 6 pages.
Non-Final Office Action mailed on Jun. 29, 2023, for U.S. Appl. No. 17/479,873, filed Sep. 20, 2021, 10 pages.
Non-Final Office Action mailed on Mar. 5, 2024, for U.S. Appl. No. 17/479,873, filed Sep. 20, 2021, 11 pages.
Notice of Allowance mailed on Oct. 16, 2023, for U.S. Appl. No. 17/566,212, filed Dec. 30, 2021, 12 pages.
Notice of Allowance mailed on Dec. 28, 2023, for U.S. Appl. No. 16/887,852, filed May 29, 2020, 9 pages.
Notice of Allowance mailed on Jan. 15, 2025, for U.S. Appl. No. 17/479,873, filed Sep. 20, 2021, 9 pages.
Notice of Allowance mailed on Feb. 19, 2025, for U.S. Appl. No. 17/479,873, filed Sep. 20, 2021, 5 pages.
Samant, S.S. et al. (Dec. 2002). "Verification of multileaf collimator leaf positions using an electronic portal imaging device," Med. Phys. 29(12):2900-2912.
Written Opinion of the International Searching Authority mailed on May 9, 2023, for PCT Application No. PCT/US2022/082375, filed on Dec. 23, 2022, 5 pages.
Written Opinion of the International Searching Authority mailed on Jun. 6, 2024, for PCT Application No. PCT/US2023/085347, filed on Dec. 21, 2023, 10 pages.

METHODS FOR RADIATION DELIVERY QUALITY ASSURANCE

CROSS-REFERENCE TO RELATED APPLICATIONS

This application claims priority to U.S. Provisional Patent Application No. 63/294,047 filed Dec. 27, 2021, the disclosure of which is hereby incorporated by reference in its entirety.

BACKGROUND

A radiotherapy treatment plan seeks to direct a prescribed dose of radiation to one or more tumors while limiting the irradiation of healthy tissue. Treatment planning uses planning CT and/or PET images and clinician-defined tumor contours to consider each patient's unique anatomy and the pathology of their cancer, and generates a radiation fluence map that would result in a cumulative therapeutic dose of radiation to the tumor while not exceeding irradiation safety thresholds for radiation-sensitive structures, such as organs at risk (OARs). A radiation fluence map specifies the radiation beamlets (e.g., size, shape, intensity, etc.) for each radiation firing position and/or patient platform position that would result in the desired dose distribution. The treatment plan fluence map is then translated (i.e., segmented) into radiotherapy machine instructions which, if executed precisely with the patient positioned in the specified location, would deliver the prescribed dose to the tumor. Radiotherapy machine instructions may include, but are not limited to, the configuration of any radiation beam-shaping components (e.g., the leaf positions of a multi-leaf collimator), the gantry angle (firing position), linear position of the patient and the number of beamlet pulses or monitor units emitted by the therapeutic radiation source (e.g., linear accelerator or linac) for each firing position.

After a treatment plan fluence map is generated, it is evaluated to confirm that it would result in the prescribed dose delivery. One method of evaluating whether a plan fluence map delivers a desired dose distribution (i.e., treatment plan quality assurance or QA) is by running a simulation using radiotherapy system models, patient models, and/or beam models to calculate an approximation of the delivered dose distribution. The simulated delivered dose distribution is compared to the desired dose distribution, and a clinician may evaluate whether the differences are acceptable. Another method for evaluating whether a plan fluence map delivers a prescribed dose is by actually delivering the plan fluence map using the segmented machine instructions without a patient in the treatment area. The delivered radiation fluence may be measured by fluence measurement devices placed in the treatment area. Radiotherapy systems that use a linac may also comprise an MV detector located opposite the linac. In these radiotherapy systems, the delivered radiation fluence may be measured by the MV detector. The measurements of the delivered radiation fluence (from one or more of the fluence measurement devices and the MV detector) may be used to reconstruct a delivered dose distribution, which is evaluated against the desired dose distribution. The results of treatment plan and delivery QA may be used to confirm whether the treatment plan delivers the prescribed dose and/or whether the radiotherapy system is capable of precisely emitting radiation according to the plan fluence map. Such treatment plan and radiation delivery QA session(s) are important for ensuring patient safety. Accordingly, it is desirable to have improved methods for evaluating a patient treatment plan and radiation delivery (i.e., in a quality assurance or QA session).

SUMMARY

Disclosed herein are methods for evaluating the quality of radiation delivery according to a treatment plan fluence map. The method may be used in therapeutic or non-therapeutic applications. One variation of evaluating the quality of radiation delivery comprises generating a simulated MV detector image of radiation emitted according to the treatment plan fluence map using acquired MV detector imaging data of different multi-leaf collimator (MLC) configurations, delivering radiation according to the treatment plan fluence map while acquiring MV detector imaging data of the delivered radiation, and comparing the acquired MV detector imaging data with the simulated MV detector image to identify any differences. The radiation may be delivered to a phantom placed in the field of view of the MV detector as part of a non-therapeutic application, for example during a QA session. The simulated MV detector image may be generated by acquiring MV detector imaging data of a single MLC leaf opening for each MLC leaf, acquiring MV detector imaging data of a double MLC leaf opening for each MLC leaf pair, segmenting a treatment plan fluence map to obtain a pattern of MLC openings, and combining the MV detector imaging data of single MLC openings and double MLC leaf openings according to the pattern of MLC openings. This method facilitates the generation of an accurate, simulated MV detector image that encompasses the intricacies of a patient-specific treatment plan fluence map while using a small set of empirical MV detector data. Reducing the amount of data collected may help expedite the QA session. Reducing the amount of time the radiotherapy system is used for QA purposes may help increase the amount of time the radiotherapy system is used for treating patients.

One variation of a method (which may be used in a non-therapeutic application) for generating a radiation detector image that corresponds to a treatment plan fluence map multi-leaf opening pattern may include acquiring imaging data of a single leaf opening using a radiation source and a radiation detector for each leaf of a multi-leaf collimator (MLC), acquiring imaging data of a double leaf opening using the radiation source and the radiation detector for each leaf of the MLC, segmenting a treatment plan fluence map into a pattern of MLC openings, and generating a radiation detector image that corresponds to the treatment plan fluence map by combining the acquired imaging data of single leaf and double leaf openings according to the pattern of MLC openings. The method may further include generating a graphical representation that comprises the generated radiation detector image and outputting the graphical representation to a display device. Optionally, the method may include calculating a radiation dose to a phantom based on the generated radiation detector image. In some variations, the radiation detector may be an MV detector or a kV detector. The radiation source and radiation detector may be mounted on a gantry rotatable to multiple firing positions, and acquiring imaging data of a single leaf opening and a double leaf opening may include rotating the gantry to a first firing position and acquiring imaging data of a single leaf opening and a double leaf opening at the first firing position, and rotating the gantry to a second firing position and acquiring imaging data of a single leaf opening and a double leaf opening at the second firing position. The method may further include acquiring imaging data of single leaf openings and double leaf openings for each leaf of the MLC at the first firing position and optionally, may include acquiring imaging data of single leaf openings and double leaf openings for each leaf of the MLC at the second firing position. The pattern of MLC openings may include a plurality of MLC leaf instructions designating leaf positions for each MLC leaf, or the pattern of MLC openings may include a plurality of single leaf openings and a plurality of double leaf openings. In some variations, combining the acquired imaging data may include summing the acquired imaging data of single leaf openings and the acquired imaging data of double leaf openings, and subtracting the imaging data of single leaf openings from areas of overlap in summed imaging data of double leaf openings. Methods may further include placing a phantom within a field of view of the radiation detector before acquiring radiation detector imaging data of single MLC leaf openings and double MLC leaf openings. Optionally, some variations may include placing a radiation fluence measurement device within a field of view of the radiation detector before acquiring radiation detector imaging data of single MLC leaf openings and double MLC leaf openings, or placing a radiation fluence measurement device within a field of view of the radiation detector before acquiring radiation detector imaging data of single MLC leaf openings and double MLC leaf openings. The acquired imaging data of single leaf openings, the acquired imaging data of double leaf openings, the pattern of MLC openings, and the generated radiation detector images may be stored in a processor memory of a radiation delivery system.

In another variation, a method may further include calculating a fill-in profile for each pair of adjacent MLC leaves by subtracting the imaging data of the two single MLC leaf openings from the imaging data of the corresponding double MLC leaf opening. Generating a radiation detector image that corresponds to the treatment plan fluence map may include combining the acquired imaging data of single leaf openings and fill-in profiles according to the pattern of MLC openings. Combining the acquired imaging data of single leaf openings and the fill-in profiles may include summing the acquired imaging data of single leaf openings and the fill-in profiles for adjacent single leaf openings. Generating the radiation detector image may further include combining acquired imaging data of double leaf openings with the imaging data of single leaf openings and fill-in profiles. Some variations may include generating a graphical representation of the generated radiation detector image and outputting the graphical representation to a display device. Optionally, the method may include calculating a radiation dose to a phantom based on the generated radiation detector image. In some variations, the radiation detector may be an MV detector or a kV detector. The radiation source and radiation detector may be mounted on a gantry rotatable to multiple firing positions, and acquiring imaging data of a single leaf opening and a double leaf opening may include rotating the gantry to a first firing position and acquiring imaging data of a single leaf opening and a double leaf opening at the first firing position, and rotating the gantry to a second firing position and acquiring imaging data of a single leaf opening and a double leaf opening at the second firing position. The method may further include acquiring imaging data of single leaf openings and double leaf openings for each leaf of the MLC at the first firing position and optionally, may include acquiring imaging data of single leaf openings and double leaf openings for each leaf of the MLC at the second firing position. The pattern of MLC openings may include a plurality of MLC leaf instructions designating leaf positions for each MLC leaf, or the pattern of MLC openings may include a plurality of single leaf openings and a plurality of double leaf openings. Optionally, some methods may include placing a phantom within a field of view of the radiation detector before acquiring radiation detector imaging data of single MLC leaf openings and double MLC leaf openings, or placing a radiation fluence measurement device within a field of view of the radiation detector before acquiring radiation detector imaging data of single MLC leaf openings and double MLC leaf openings. The acquired imaging data of single leaf openings, the acquired imaging data of double leaf openings, the pattern of MLC openings, and the generated radiation detector images may be stored in a processor memory of a radiation delivery system.

Also disclosed herein are methods for evaluating the quality of radiation delivery. The method may be used in therapeutic or non-therapeutic applications. One variation may include generating a simulated radiation detector image corresponding to a treatment plan fluence map using imaging data of single leaf openings and double leaf openings of an MLC, delivering radiation according to the treatment plan fluence map using the therapeutic radiation source of a radiotherapy system, acquiring radiation detector imaging data during radiation delivery to generate a radiation detector image, determining image differences between the acquired radiation detector image and the simulated radiation detector image, and generating a graphical representation that depicts the image differences between the acquired radiation detector image and simulated radiation detector image. The method may include generating a notification if the image differences are greater than an acceptable threshold. The radiotherapy system may include a patient area and the method may further include placing a phantom in the patient area before delivering radiation, for example when the method is used in a non-therapeutic application. Alternatively, or additionally, the radiotherapy system may include a patient area and the method may further include placing a radiation fluence measurement device in the patient area before delivering radiation. Some variations may further include calculating a simulated dose based on the simulated radiation detector image, calculating a delivered dose based on the acquired radiation detector image, determining dose differences between the simulated dose and the delivered dose, and generating a graphical representation that depicts the dose differences. The method may include generating a notification if the dose differences are greater than an acceptable threshold. Optionally, a method may further include updating radiation delivery parameters if the differences are greater than an acceptable threshold.

Another variation of a method for generating a radiation detector image that corresponds to a treatment plan fluence map may include acquiring, for each leaf of a multi-leaf collimator, imaging data of a single leaf opening and a double leaf opening using a radiation source and a radiation detector, and combining the acquired imaging data to generate a radiation detector image to match a pattern of MLC openings that correspond with a treatment plan fluence map. The method may be used in non-therapeutic applications. The method may further include generating a graphical representation that comprises the generated radiation detector image and outputting the graphical representation to a display device. In some variations, the radiation detector may be an MV detector or a kV detector. The radiation source and radiation detector may be mounted on a gantry rotatable to multiple firing positions, and acquiring imaging data of a single leaf opening and a double leaf opening may include rotating the gantry to a first firing position and acquiring imaging data of a single leaf opening and a double leaf opening at the first firing position, and rotating the gantry to a second firing position and acquiring imaging data of a single leaf opening and a double leaf opening at the second firing position. The method may further include acquiring imaging data of single leaf openings and double leaf openings for each leaf of the MLC at the first firing position and optionally, may include acquiring imaging data of single leaf openings and double leaf openings for each leaf of the MLC at the second firing position. The pattern of MLC openings may include a plurality of MLC leaf instructions designating leaf positions for each MLC leaf, or the pattern of MLC openings may include a plurality of single leaf openings and a plurality of double leaf openings. The acquired imaging data of single leaf openings, the acquired imaging data of double leaf openings, the pattern of MLC openings, and the generated radiation detector images are stored in a processor memory of a radiation delivery system. Combining the acquired imaging data may include summing the acquired imaging data of single leaf openings and the acquired imaging data of double leaf openings, and subtracting the imaging data of single leaf openings from areas of overlap in summed imaging data of double leaf openings. Alternatively, or additionally, a method may further include calculating a fill-in profile for each pair of adjacent MLC leaves by subtracting the imaging data of the two single MLC leaf openings from the imaging data of the corresponding double MLC leaf opening and wherein combining the acquired imaging data to generate the radiation detector image comprises combining the acquired imaging data of single leaf openings and fill-in profiles according to the pattern of MLC openings. In some variations, combining the acquired imaging data of single leaf openings and fill-in profiles may include summing the acquired imaging data of single leaf openings and the fill-in profiles for adjacent single leaf openings. In some variations, combining the acquired imaging data to generate the radiation detector image may include combining the double leaf openings with the imaging data of single leaf openings and fill-in profiles. Optionally, some methods may further include generating a graphical representation of the generated radiation detector image and outputting the graphical representation to a display device While the examples provided herein are in the context of generating simulated MV detector images and using those simulated images for the purposes of treatment plan delivery QA, it should be understood that similar methods may be used for generating simulated images for other imaging modalities (e.g., kV CT, kV planar imaging or kV radiation delivery systems) using other types of radiation detectors. The methods described herein may be used for purposes other than treatment plan delivery QA. For example, a small animal treatment system may use a kV radiation source with an MLC. Similarly, specialized radiotherapy systems for skin or eye treatments may also use lower kV energy radiation sources coupled with an MLC; the systems and methods disclosed herein may also be used with such treatment systems.

DETAILED DESCRIPTION

Disclosed herein are methods for generating MV detector images that are specific to a patient's treatment plan fluence map and using the generated MV detector images to evaluate the ability of a radiotherapy system to deliver the plan fluence map. The MV detector images simulate the image(s) and/or imaging data that would have been acquired on an MV detector if radiation was precisely emitted by the therapeutic radiation source (e.g., linac) and shaped by a multi-leaf collimator (MLC) according to the treatment plan fluence map. The MV detector images may be generated using MV detector imaging data acquired on a radiotherapy system. In some variations, the acquired MV detector imaging data may be of a limited number of MLC configurations, for example, single leaf openings and/or double leaf openings for each leaf of the MLC. This limited set of imaging data may be combined as described herein to generate MV detector images that correspond with a patient's treatment plan fluence map. Limiting the amount of MV detector imaging data acquired on a radiotherapy system may help reduce the amount of time that the radiotherapy system is used for QA purposes and increase the availability of the radiotherapy system for treating patients.

The MV detector images generated using acquired MV detector imaging data may be used to evaluate how well a radiotherapy system delivers radiation according to the plan fluence map. For example, methods for evaluating the quality of radiation delivery of a radiotherapy system may comprise delivering or emitting radiation according to the treatment plan fluence map, acquiring MV detector imaging data during the radiation delivery, and comparing the acquired MV detector image with the generated MV detector image that simulates the delivery of the treatment plan fluence map.

The methods described herein may be used to generate MV detector images for any radiotherapy system comprising an MV detector, and is not limited to the particular radiotherapy systems described and depicted below. For example, the methods for acquiring MV detector imaging data and generating MV detector images may be used with any radiotherapy system comprising a therapeutic radiation source that emits high-energy X-rays and an MV detector located across from (e.g., opposite) the therapeutic radiation source. The therapeutic radiation source and MV detector may be mounted on a circular gantry, or a C-arm gantry, or a robotic arm, which may comprise one or more motion systems configured to position the therapeutic radiation source at various firing positions around the patient area. Alternatively, or additionally, the methods described herein may be used for generating any X-ray detector images (e.g., kV CT images) based on a limited set of empirically acquired detector imaging data (e.g., kV CT imaging data).

Radiotherapy System

Figure 1A:
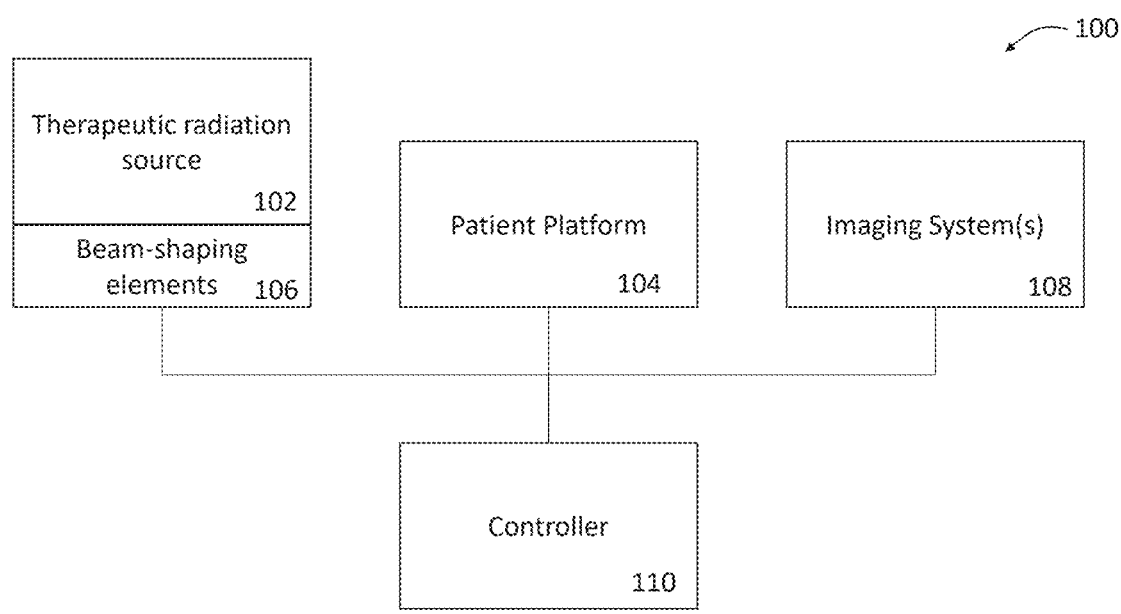
FIG. 1A is a functional block diagram of a variation of a radiotherapy system.
Figure 1B:
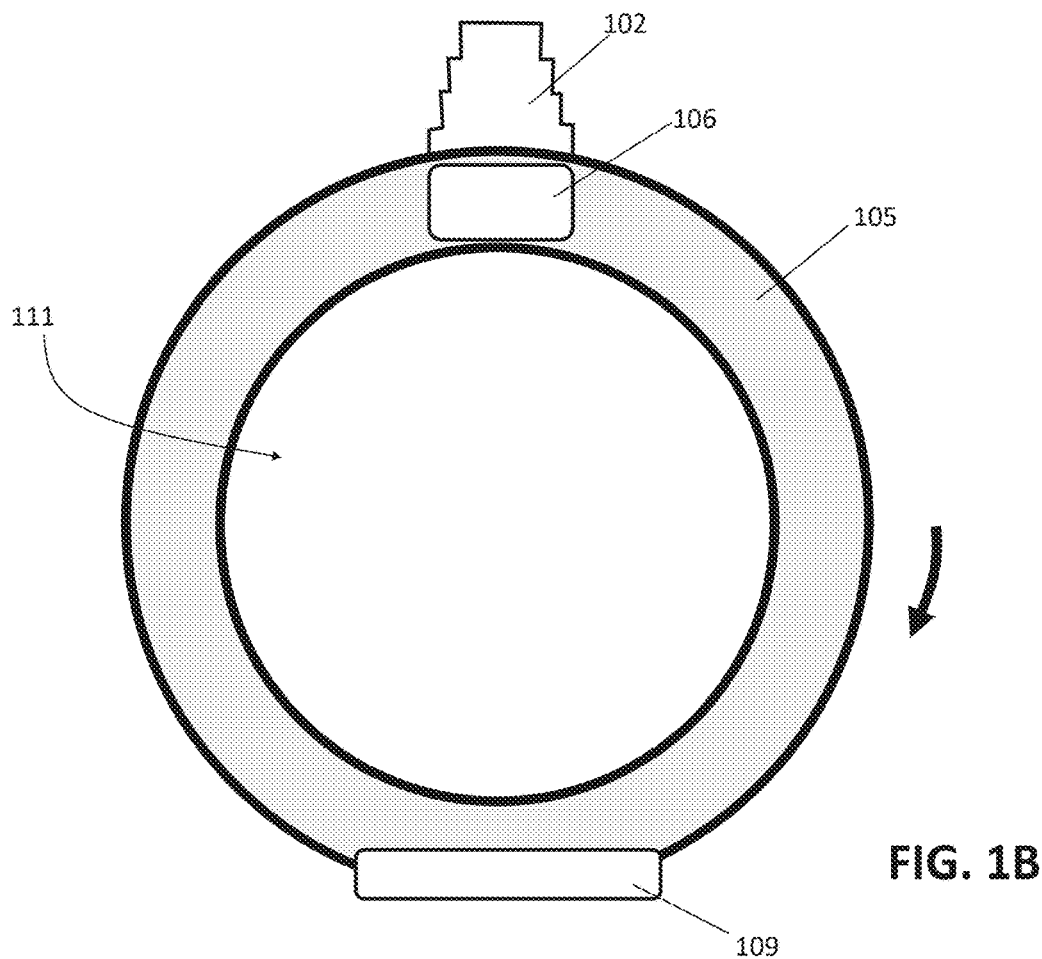
FIGS. 1B and 1C are schematic representations of one variation of a radiotherapy system comprising a rotatable gantry, a linac, a beam-shaping assembly, and an MV detector.
Figure 1C:
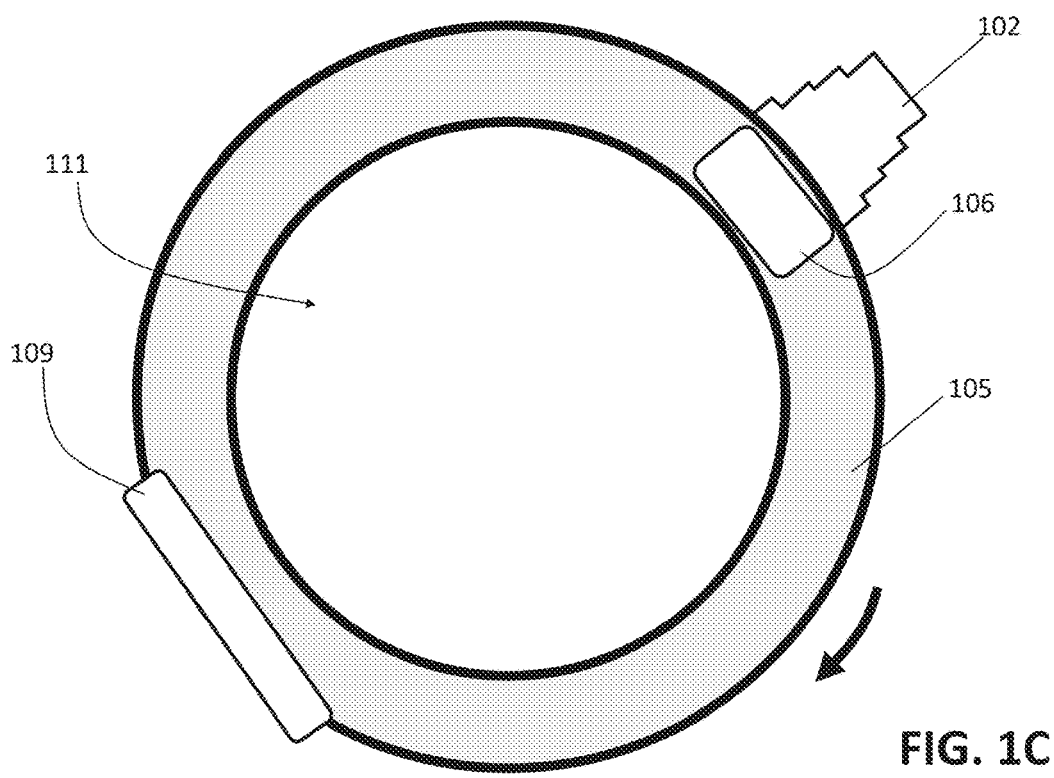

FIG. 1A depicts a functional block diagram of a variation of a radiotherapy system that may be used with one or more of the methods described herein. Radiotherapy system (100) comprises one or more therapeutic radiation sources (102) and a patient platform (104). The therapeutic radiation source may comprise an X-ray source, electron source, proton source, and/or a neutron source. For example, a therapeutic radiation source (102) may comprise a linear accelerator (linac), Cobalt-60 source, and/or an X-ray machine. The therapeutic radiation source may be movable about the patient platform so that radiation beams may be directed to a patient on the patient platform from multiple firing positions and/or angles. In some variations, a radiotherapy system may comprise one or more beam-shaping elements and/or assemblies (106) that may be located in the beam path of the therapeutic radiation source. For example, a radiotherapy system may comprise a linac (102) and a beam-shaping assembly (106) disposed in a path of the radiation beam. The beam-shaping assembly may comprise one or more movable jaws and one or more collimators. At least one of the collimators may be an MLC comprising a plurality of individually-controlled leaves. The MLC may be a 1-D MLC (i.e., a binary MLC where each leaf is either open or closed). The linac and the beam-shaping assembly may be mounted on a gantry or movable support frame that comprises a motion system configured to adjust the position of the linac and the beam-shaping assembly. In some variations, the linac and beam-shaping assembly may be mounted on a support structure comprising one or more robotic arms, C-arms, gimbals, and the like. The patient platform (104) may also be movable. The radiotherapy system (100) may comprise one or more imaging systems (108) of one or more imaging modalities. For example, the one or more imaging systems (108) may comprise a kV CT imaging system, a PET imaging systems, an MV X-ray imaging system, and/or an MR imaging system. The imaging systems (108) may be coplanar with the treatment plane of the therapeutic radiation source, while in other variations, the imaging systems (108) may not be coplanar with the treatment plane. For example, the imaging plane(s) of a PET imaging system and/or MR imaging system and/or MV X-ray imaging system may be coplanar with the treatment plane while the kV CT imaging system may have an imaging plane that does not coincide with the treatment plane. In some variations, an MV X-ray imaging system may comprise an MV detector that is mounted on the gantry and located opposite the linac and beam-shaping assembly. FIG. 1B is a schematic representation of one variation of a radiotherapy system comprising a rotatable gantry (105), and a linac (102), beam-shaping assembly (106), and MV detector (109) mounted on the gantry (105). The MV detector is directly across from (i.e., opposite) the linac and the beam-shaping assembly. The gantry (105) may be continuously rotatable in one direction (as represented by the arrow), or may be rotatable in both clockwise and counter-clockwise directions, as may be desirable. The beam-shaping assembly (106) may include an MLC, such as any MLC described herein. Rotating the gantry (105) may move the linac (102) to various firing position (e.g., firing angles) around the treatment area (111). As shown in FIG. 1C, when the gantry rotates to move the linac to a new firing position, the beam-shaping assembly and MV detector also move in a corresponding fashion. While the radiotherapy system depicted here includes a circular gantry, it should be understood that the radiotherapy system may instead include one or more robotic arms, C-arms, and gimbals.

Radiation that is emitted by the linac and shaped by the MLC (and/or in combination with any components of the beam-shaping assembly) may be measured by the MV detector. The imaging data or measurements acquired by the MV detector may be used to detect the size and shape of the MLC opening cumulatively formed by the positions of the leaves. For example, MV detector imaging data may be used to determine whether an MLC leaf of a binary MLC is open or closed, determine the shape of the MLC opening, and/or calculate the radiation fluence that has passed through the MLC opening. When a treatment plan fluence map is segmented into machine instructions, the machine instructions may comprise MLC leaf instructions that designate the position of each leaf for each firing position of the therapeutic radiation source, over one or more patient platform locations. These machine instructions may be used in a quality assurance (QA) procedure to evaluate the performance of the radiotherapy system. The configuration of the MLC (i.e., shape of the MLC opening as a result of the position of each of the MLC leaves) as measured by the MV detector may be compared with the MLC leaf instructions derived from the treatment plan fluence map. The MV detector imaging data may be used, for example, to evaluate the precision of MLC leaf actuation as the MLC steps through each pattern or configuration as specified by the machine instructions segmented from the treatment plan fluence map.

A radiotherapy system (100) may comprise a controller (110) that is in communication with the therapeutic radiation source (102), beam-shaping elements or assemblies (106), patient platform (104), one or more image sensors (108) (e.g., one or more imaging systems), and the one or more fluence measurement devices (101). The controller (110) may comprise one or more processors and one or more machine-readable memories in communication with the one or more processors, which may be configured to execute or perform any of the methods described herein. The controller may record and store information generated during the delivery of radiation (e.g., in a treatment session and/or quality assurance session) including beam energy, monitor units, MLC and patient platform data (e.g., patient platform position coordinates), images taken during delivery, etc. in the machine-readable memory. The one or more machine-readable memories may store instructions to cause the processor to execute modules, processes and/or functions associated with the system, such as one or more treatment plans, system calibration procedures, system quality assurance (QA) procedures, the calculation of radiation fluence maps based on treatment plan and/or clinical goals, segmentation of fluence maps into radiotherapy system instructions (e.g., that may direct the operation of the gantry, therapeutic radiation source, beam-shaping assembly, patient platform, and/or any other components of a radiotherapy system), and image and/or data processing associated with treatment planning and/or radiation delivery. In some variations, the memory may store treatment plan data (e.g., treatment plan firing filters, fluence map, planning images, treatment session PET pre-scan images and/or initial CT, MRI, and/or X-ray images). In some variations, the controller may be configured to compare data acquired during a radiation delivery (e.g., acquired MV detector imaging data) with treatment plan data (e.g., expected MV detector imaging data) to evaluate how closely the actual radiation delivery matched the planned radiation delivery (e.g., a "record and verify" system). The controller of a radiotherapy system may be connected to other systems by wired or wireless communication channels. For example, the radiotherapy system controller may be in wired or wireless communication with a radiotherapy treatment planning system controller such that fluence maps, firing filters, initial and/or planning images (e.g., CT images, MRI images, PET images, 4-D CT images), patient data, and other clinically-relevant information may be transferred from the radiotherapy treatment planning system to the radiotherapy system. The delivered radiation fluence, any dose calculations, and any clinically-relevant information and/or data acquired during a QA and/or treatment session may be transferred from the radiotherapy system to the radiotherapy treatment planning system. This information may be used by the radiotherapy treatment planning system for adapting the treatment plan and/or adjusting delivery of radiation for a successive treatment session. Additional descriptions of radiotherapy systems are provided in U.S. Pat. No. 10,695,586 filed Nov. 15, 2017, which is hereby incorporated by reference in its entirety.

Quality Assurance (QA) Methods

After a treatment plan fluence map is generated, it may be evaluated to confirm that it provides the desired (e.g., prescribed) dose distribution and that the radiotherapy system is able to deliver the plan fluence map precisely and accurately. One variation of a method of evaluating whether the radiotherapy system is able to deliver the plan fluence map may comprise using the linac and MLC of the radiotherapy system to emit radiation according to the plan fluence map, measuring the emitted radiation by acquiring imaging data on the MV detector, generating an MV detector image from the acquired imaging data, and comparing the generated MV detector image with an expected MV detector image. The expected MV detector image may represent the MV detector imaging data that would have been acquired if the radiotherapy system were able to successfully execute the machine instructions from the segmented treatment plan fluence map. In some variations, the expected MV detector image may be generated from a simulation using radiation beam models and radiotherapy system component models, for example, MLC models that simulate how radiation interacts with the MLC leaves, how the tongue-and-groove (TNG) effect affects the radiation fluence, and/or radiation scatter from the MLC leaves. Alternatively, or additionally, the expected MV detector image may be generated by combining empirical MV detector imaging data in accordance with the machine instructions derived from segmenting the treatment plan fluence map. For a binary MLC, this may entail acquiring MV detector data for every MLC configuration, for example, a single leaf opening, a double leaf opening, a triple leaf opening, and so on, for MLC openings of any number of leaves, for every leaf in the MLC. For example, in the variation where a radiotherapy system has a 64-leaf binary MLC, MV detector imaging data may be acquired for a single leaf opening (for leaves #1-64), a double leaf opening (for leaves #1-63), a triple leaf opening (for leaves #1-62), and so forth, up to and including a 63-leaf opening (for leaves #1 and #2) and a 64-leaf opening (for leaf #1). The acquired MV detector imaging data may then be combined together to form the MV detector image that corresponds to any arbitrary pattern of MLC openings, including the pattern of MLC openings that correspond with a treatment plan fluence map developed for a particular patient.

However, this method of acquiring MV detector imaging data may be time consuming and occupy the treatment bunker and radiotherapy system for longer than may be desired for a non-treatment purpose. As an example, for a 64-leaf binary MLC, for each firing position (e.g., firing angle around a circular gantry), the MLC needs to step through a total of 2080 MLC leaf patterns while emitting radiation from the linac and acquiring MV detector data for each MLC leaf pattern. The number of MLC leaf patterns for which the MV detector needs to be acquired in order to be able to generate any arbitrary pattern of MLC openings may increase for MLCs with more leaves.

The methods described herein may comprise acquiring MV detector imaging data for a limited number of MLC patterns or configurations using this limited set of MV detector imaging data to generate an expected MV detector image (which may also be referred to as a simulated MV detector image) for radiation delivery QA. In one variation, the method may comprise acquiring MV detector imaging data for only single leaf openings and double leaf openings. This may help to reduce the amount of time that the radiotherapy system is used for a QA session (i.e., a non-treatment purpose). As an example, for a 64-leaf binary MLC, the methods described herein may comprise acquiring MV detector imaging data of a single leaf opening for 64 leaves, and acquiring MV detector imaging data of a double leaf opening for 63 leaves. To acquire this MV detector imaging data, the MLC needs to step through a total of 127 MLC leaf patterns while emitting radiation from the linac and acquiring MV detector data for each MLC leaf pattern. These 127 MV detector images of these MLC leaf patterns may be combined (e.g., summed and/or subtracted) to create the MV detector image of an arbitrary MLC leaf pattern, such as the MLC leaf pattern that corresponds to a patient's treatment plan fluence map. This expected MV detector image may then be used to evaluate the quality of an actual radiation delivery of a treatment plan fluence map during a QA session (i.e., in the absence of a patient).

In one variation, an MV detector image of an arbitrary MLC leaf pattern may be generated from single leaf openings and double leaf openings by summing the MV detector imaging data of double leaf openings that overlap each other (i.e., overlap areas for certain MLC leaves) and subtracting the MV detector imaging data of single leaf openings to remove the overlap. In another variation, an MV detector image of an arbitrary MLC leaf pattern may be generated from single leaf openings and double leaf openings by calculating a fill-in profile between each leaf of the MLC (e.g., using the acquired single leaf opening and double leaf opening MV detector imaging data), and then summing single leaf opening MV detector imaging data with the corresponding fill-in profile(s). These methods may help compensate for the tongue-and-groove artifact that could arise from summing single leaf openings.

Figure 2:
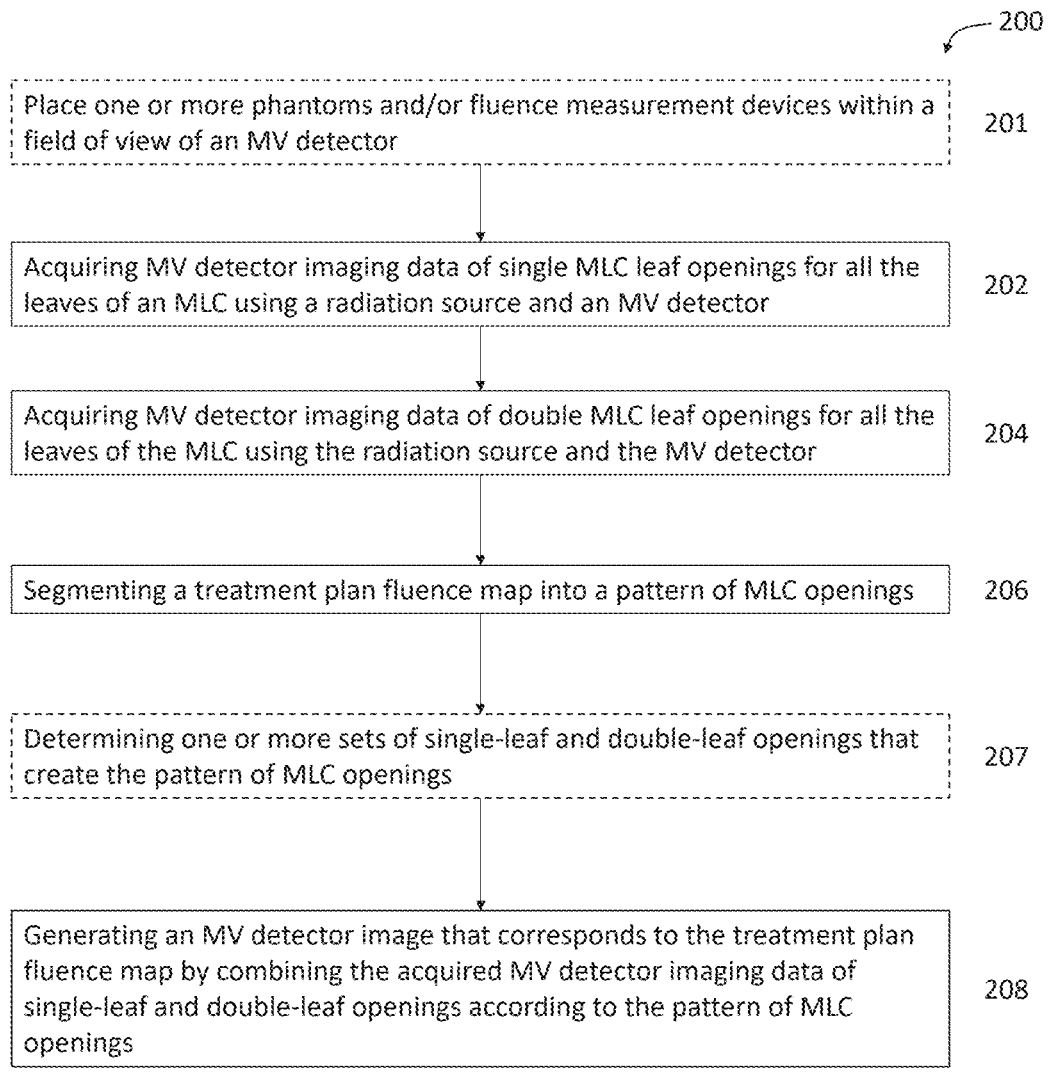
FIG. 2 is a flowchart representation of one variation of a method for generating an MV detector image using acquired MV detector imaging data of different MLC configurations.
Figure 3A:
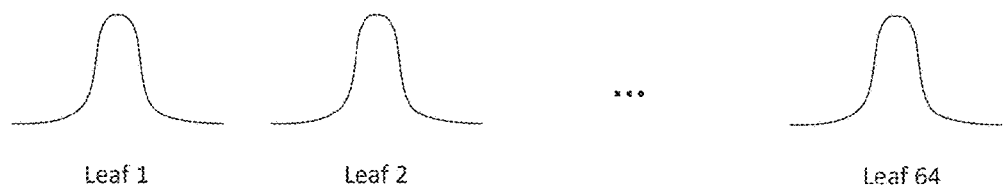
FIGS. 3A-3D are conceptual depictions of single leaf opening and double leaf opening MV detector imaging data, and one example of how they may be combined to simulate an MV detector image corresponding to a desired pattern of MLC openings according to the method depicted in FIG. 2.
Figure 3B:
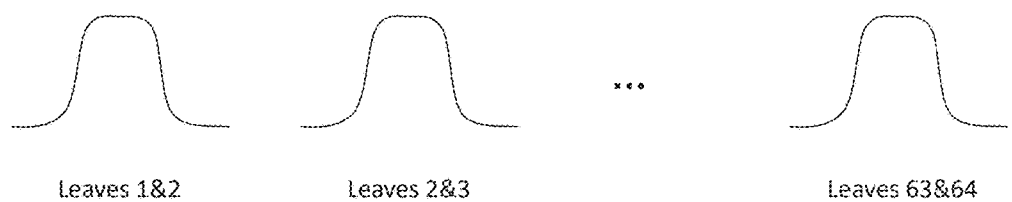

FIG. 2 is a flowchart representation of one variation of a method for generating an expected MV detector image (also referred to as a simulated MV detector image) that may be used to evaluate the radiation delivery of a patient-specific treatment plan fluence map. Method (200) may comprise acquiring (202) MV detector imaging data of single MLC leaf openings for all the leaves of an MLC using a radiation source and an MV detector, acquiring (204) MV detector imaging data of double MLC leaf openings for all the leaves of the MLC using the radiation source and the MV detector, segmenting (206) a treatment plan fluence map into a pattern of MLC openings, and generating (208) an MV detector image that corresponds to the treatment plan fluence map by combining the acquired MV detector imaging data of single-leaf and double-leaf openings according to the pattern of MLC openings. In some variations, steps (201-204) may be performed on a radiotherapy system comprising a linac, MLC, MV detector and a radiotherapy system controller (e.g., the radiotherapy system described above), while steps (206-208) may be performed using the radiotherapy system controller and/or a separate controller (e.g., a controller of a treatment planning or treatment QA system). Alternatively, or additionally, a radiotherapy system may comprise one or more controllers, at least one of which may be in communication with the linac, MLC, and MV detector, and at least one of the other controllers may be configured to perform one or more of the steps in method (200). For example, a first radiotherapy system controller may be configured to perform steps (201-204) while a second radiotherapy system controller may be configured to perform steps (206-208). The generated MV detector image (which may also be referred to as an expected MV detector image or a simulated MV detector image) may be used to evaluate the delivery of a treatment plan. FIG. 3A depicts an example of MV detector imaging data of single MLC leaf openings for a binary MLC with 64 leaves. During the acquisition (202) of MV detector imaging data for single leaf openings, the MLC opens one leaf at a time, from leaf 1 to leaf 64, and emits radiation from the linac and records the imaging data for that single leaf opening. FIG. 3B depicts an example of MV detector imaging data of double MLC leaf openings for a binary MLC with 64 leaves. During the acquisition (204) of MV detector imaging data for double leaf openings, the MLC opens two adjacent leaves at a time, from leaf 1 to leaf 63 (since a double leaf opening at leaf 64 includes leaf 63), and emits radiation from the linac and records the imaging data for that double leaf opening. Optionally, for radiotherapy systems comprising a rotatable gantry or arm that are configured to move the linac to multiple firing positions, a different set of single-leaf openings and double-leaf openings may be acquired for each firing position. As an example, for a radiotherapy system comprising 50 firing positions, method (200) may comprise repeating steps (202-204) 50 times. That is, the gantry may move (e.g., rotate) the linac to a first firing position, MV detector imaging data may be acquired for single-leaf and double-leaf openings as described above, then the linac may be linac to a second firing position, MV detector imaging data may be acquired for single-leaf and double-leaf openings at this second firing position, and so on. The MV detector imaging data acquired in steps (202-204) may be stored in a processor memory of a radiotherapy system and/or treatment planning system. In some variations where it is expected that the radiation emitted from the linac has a consistent profile and only one set of single-leaf openings and double-leaf openings may be acquired, regardless of the number of linac firing positions.

A fluence map may comprise a set of radiation beamlets and beamlet intensities for one or more linac firing positions that delivers a desired dose. Segmenting a plan fluence map may comprise translating the set of beamlets and intensities into MLC leaf instructions and/or linac firing instructions for each firing position of the linac. A segmented fluence map may, for example, indicate which MLC leaves are to be opened (and which are to be closed) at a given firing position. In some variations, a pattern of MLC leaves comprises a plurality of MLC leaf instructions designating leaf positions for each MLC leaf. The pattern of MLC leaves shapes the radiation that passes through it from the linac to the MV detector. The MV detector imaging data that results from emitting radiation through a particular pattern of MLC leaves may be generated by summing the appropriate MV detector imaging data for double leaf openings and subtracting areas of overlap using the MV detector imaging data for single leaf openings for the leaves in the overlap area.

Figure 3C:
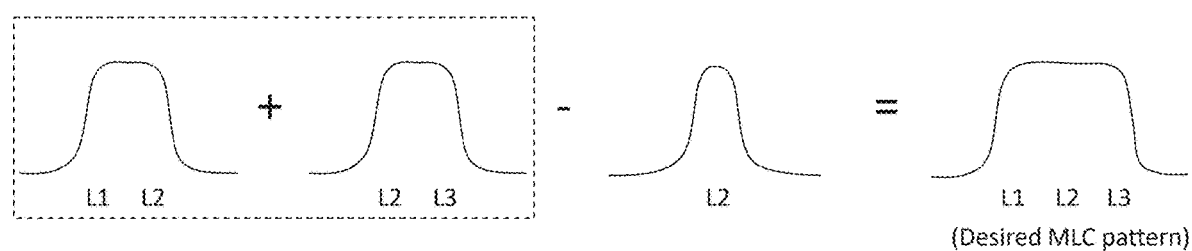
Figure 3D:
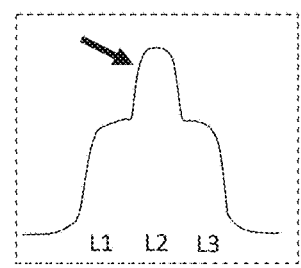

FIG. 3C depicts an example of how the acquired MV detector imaging data for single leaf openings and double leaf openings may be combined to simulate an MV detector image corresponding to a desired pattern of MLC openings. In this example, the desired MLC opening pattern is a three leaf opening across leaves 1, 2, 3. One method to determining the MV detector image corresponding to this MLC pattern is to sum the imaging data for a double leaf opening for leaf 1 and a double leaf opening for leaf 2. Because both of these two double leaf openings include leaf 2, there is an area of overlap for leaf 2. This is depicted in FIG. 3D, where the arrow points to the area of overlap on leaf 2 where the imaging data indicates a peak signal because the imaging data for leaf 2 was included twice. The method may comprise removing this area of overlap by subtracting the imaging data for a single leaf opening of leaf 2, resulting in the image corresponding to the desired MLC pattern. More generally, determining the MV detector image for an x-leaf opening (where x is from 3 to the total number of leaves in the MLC) for an i-th leaf (where i is a leaf number from 1 to the total number of leaves) may comprise summing the MV detector images of double leaf openings for leaf number(s) i, (i+1), . . . , (i+x−2) and subtracting the MV detector images of single leaf openings for leaf number(s) (i+1), (i+2), . . . , (i+x−2). For example, to determine the MV detector image for a 12-leaf opening (i.e., x=12) for the $5^{th}$ leaf (i.e., i=5), a processor may sum the MV detector images of double leaf openings for leaves 5 to 15 and subtract the MV detector images of single leaf openings for leaves 6 to 15.

Some variations of method (200) may comprise determining (207) one or more sets of single-leaf and double-leaf openings that create the pattern of MLC openings. For example, method (200) may comprise determining a first set of double-leaf openings that may be summed together and a second set of single-leaf openings that may be subtracted from the sum of double-leaf openings. The first and second sets may include all of the double-leaf openings and single-leaf openings for all of the MLC configurations that comprise the segmented fluence map for the entire treatment. For example, the first and second sets may include all of the double-leaf openings and single-leaf openings for the MLC configurations at each firing position for multiple gantry rotations (in the case of a radiotherapy system with a rotatable gantry), for multiple beam stations (i.e., multiple discrete patient platform positions at which the platform is stopped while radiation is delivered), and/or for multiple shuttle passes through the treatment beam (i.e., moving the patient platform through the treatment beam multiple times, where each instance through the treatment beam is one pass). Alternatively, or additionally, determining (207) one or more sets of single-leaf and double-leaf openings may comprise generating a set of single-leaf openings and a set of double-leaf openings for each shuttle pass. An expected MV detector image may be generated for each shuttle pass, and during treatment delivery QA, the quality of the radiation delivery may be evaluated on a pass-by-pass basis.

In some variations, method (200) may comprise placing (201) one or more phantoms and/or fluence measurement devices within a field of view of an MV detector before acquiring (202, 204) MV detector imaging data of single-leaf and double-leaf openings. The phantom(s) may comprise regions that have radiation attenuation and/or absorption properties that mimic those of patient tissue and/or tumor tissue. These MV detector imaging data of single-leaf and double-leaf openings in the presence of a phantom may be used in the same manner as the imaging data of single-leaf and double-leaf openings in the absence of a phantom. The MV detector data in the presence of a phantom may be used to generate an expected MV detector image when a treatment plan fluence map is delivered to a phantom (which may mimic or model the anatomical and/or physiological aspects of a patient and/or tumors). Alternatively, or additionally, the phantom(s) may comprise a fluence measurement device. Examples of fluence measurement devices may include, but are not limited to, a diode array, thin film transistor (TLT), thermoluminescent dosimeter (TLD), film, and/or any radiation photon detection device. The measurements acquired by the fluence measurement device(s) acquired during a radiation delivery QA session may be compared with the MV detector imaging data, and the comparison may be used to calculate a calibration factor that relates the MV detector imaging data to the measurements from the fluence measurement device(s). The calibration factor, along with the patient CT scan may be used to perform an absolute dose calculation during a radiation delivery session, e.g., a treatment session. In some variations, methods may comprise calculating a radiation dose to the phantom using the generated radiation detector image based on the acquired MV detector data and the known geometric and material properties of the phantom. After the dose delivered to the phantom is determined, the delivered dose may be evaluated using metrics such as gamma evaluation (e.g., gamma index analysis). For example, the gamma index value for various points on the test dose distribution (the delivered dose distribution to the phantom) and reference dose distribution (the expected or planned dose distribution, i.e., dose according to the treatment plan) may be calculated and compared to a passing gamma index threshold to determine whether the dose difference is acceptable. In some variations, a gamma evaluation may include determining whether the delivered dose distribution meets dose-difference (DD) and/or distance-to-agreement (DTA) criteria (e.g., 3%/3 mm) for multiple points on the distribution.

Figure 4:
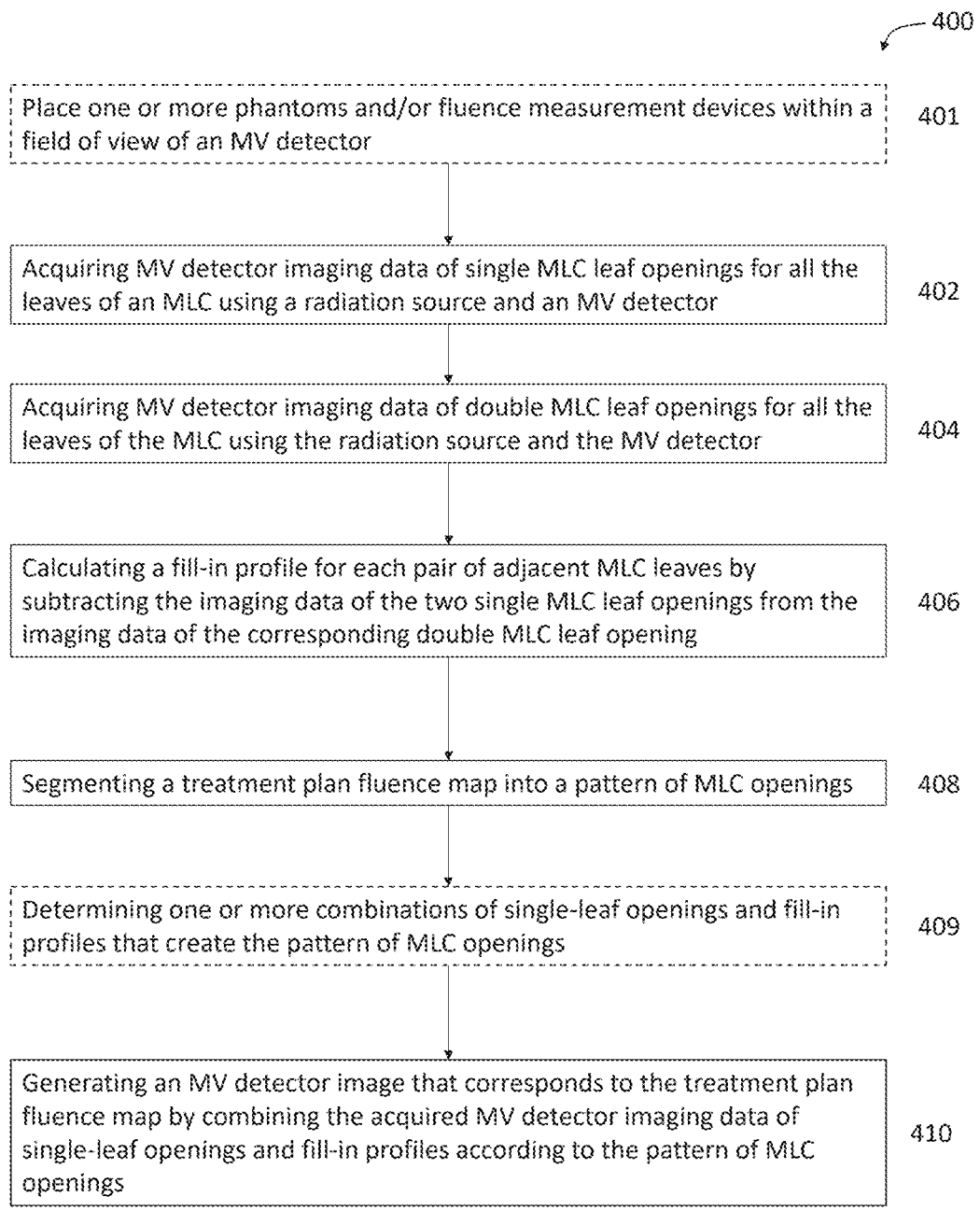
FIG. 4 is a flowchart representation of another variation of a method for generating an MV detector image using acquired MV detector imaging data of different MLC configurations.
Figure 5A:
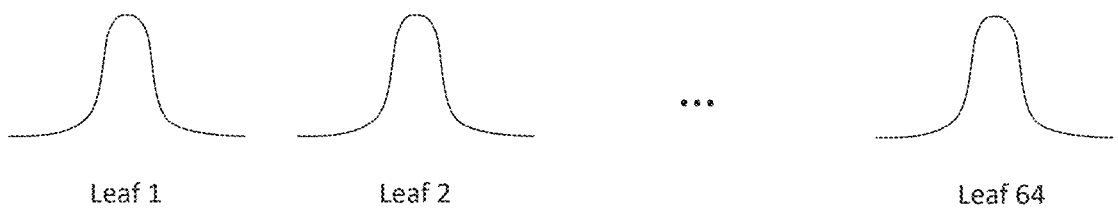
FIGS. 5A-5E are conceptual depictions of single leaf opening and double leaf opening MV detector imaging data and fill-in profiles, and one example of how they may be combined to simulate an MV detector image corresponding to a desired pattern of MLC openings according to the method depicted in FIG. 4.
Figure 5B:
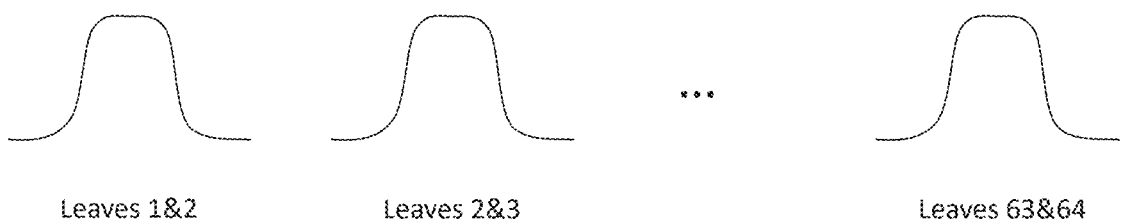

FIG. 4 is a flowchart representation of another variation of a method for generating an expected MV detector image that may be used to evaluate the radiation delivery of a patient-specific treatment plan fluence map. Method (400) may comprise acquiring (402) MV detector imaging data of single MLC leaf openings for all the leaves of an MLC using a radiation source and an MV detector, acquiring (404) MV detector imaging data of double MLC leaf openings for all the leaves of the MLC using the radiation source and the MV detector, calculating (406) a fill-in profile for each pair of adjacent MLC leaves by subtracting the imaging data of the two single MLC leaf openings from the imaging data of the corresponding double MLC leaf opening, segmenting (408) a treatment plan fluence map into a pattern of MLC openings, and generating (410) an MV detector image that corresponds to the treatment plan fluence map by combining the acquired MV detector imaging data of single leaf openings and fill-in profiles according to the pattern of MLC openings. The generated MV detector image (which may also be referred to as an expected MV detector image or a simulated MV detector image) may be used to evaluate the delivery of a treatment plan. In some variations, steps (401-404) may be performed on a radiotherapy system comprising a linac, MLC, MV detector and a radiotherapy system controller (e.g., the radiotherapy system described above), while steps (406-410) may be performed using the radiotherapy system controller and/or a separate controller (e.g., a controller of a treatment planning or treatment QA system). Alternatively, or additionally, a radiotherapy system may comprise one or more controllers, at least one of which may be in communication with the linac, MLC, and MV detector, and at least one of the other controllers may be configured to perform one or more of the steps in method (400). For example, a first radiotherapy system controller may be configured to perform steps (401-404) while a second radiotherapy system controller may be configured to perform steps (406-410). FIG. 5A depicts an example of MV detector imaging data of single MLC leaf openings for a binary MLC with 64 leaves and FIG. 5B depicts an example of MV detector imaging data of double MLC leaf openings for a binary MLC with 64 leaves. The acquisition (402, 404) of MV detector imaging data for single leaf openings and double leaf openings may be similar to that described above with regard to FIGS. 4A and 4B.

Figure 5C:
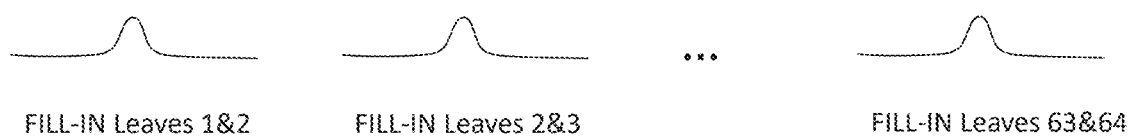
Figure 5D:
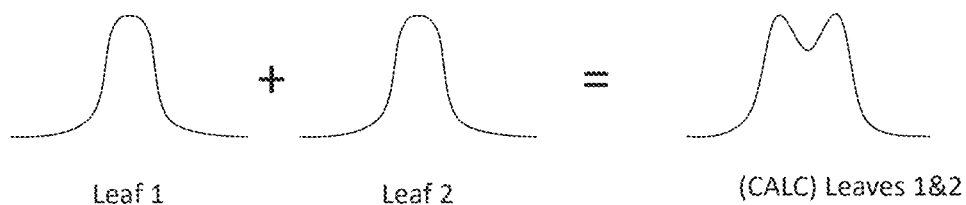
Figure 5E:
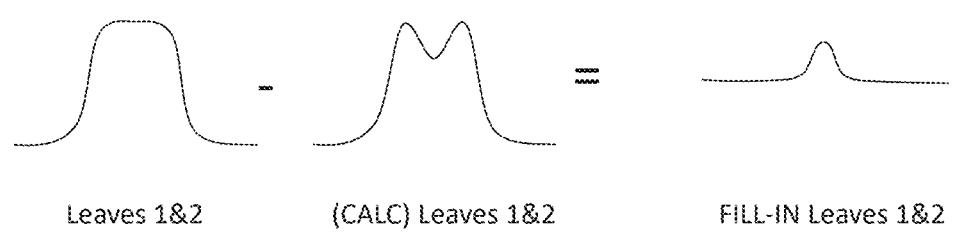

FIG. 5C depicts the fill-in profile for each pair of adjacent MLC leaves from leaves 1 and 2, all the way up to leaves 63 and 64. FIGS. 5D and 5E depict how a fill-in profile for two adjacent leaves (in this example, leaves 1 and 2) may be calculated. The MV detector imaging data for the single leaf opening for leaf 1 and the single leaf opening for leaf 2 may be summed together to obtain (CALC) leaves 1&2. Due to the leading and trailing edges of the imaging data profile for individual leaves, the sum of two single leaf openings has a region where the imaging signal is reduced, which is not accurate as compared to the corresponding acquired (404) MV detector double leaf imaging data for when leaves 1 and 2 are open. A fill-in profile is an imaging signal that compensates for the reduced imaging signal when summing the single leaf MV detector imaging data of two adjacent leaves. The fill-in profile for leaves 1&2 may be calculated by subtracting the summed single leaf imaging data of leaf 1 and leaf 2 from the double leaf imaging data of leaves 1&2, as conceptually depicted in FIG. 5E. Then, the MV detector imaging data for a double leaf opening for leaves 1 and 2 may be calculated by summing the single leaf opening imaging data for leaf 1, the single leaf opening imaging data for leaf 2, and the fill-in profile for leaves 1&2. The MV detector imaging data for any desired MLC pattern may be created using the single leaf opening imaging data for all of the leaves and the fill-in profiles for all of the adjacent leaves. For example, to generate the MV detector image for an MLC pattern where leaves 4, 5, and 6 are open, the method may comprise summing the single leaf opening imaging data for leaf 4, the single leaf opening imaging data for leaf 5, the single leaf opening imaging data for leaf 6, and two fill-in profiles (i.e., a fill-in profile for leaves 4&5 and a fill-in profile for leaves 5&6).

Optionally, for radiotherapy systems comprising a rotatable gantry or arm that are configured to move the linac to multiple firing positions, a different set of single-leaf openings and double-leaf openings may be acquired for each firing position. As an example, for a radiotherapy system comprising 50 firing positions, method (400) may comprise repeating steps (402-404) 50 times. That is, the gantry may move (e.g., rotate) the linac to a first firing position, MV detector imaging data may be acquired for single-leaf and double-leaf openings as described above, then the linac may be moved to a second firing position, MV detector imaging data may be acquired for single-leaf and double-leaf openings at this second firing position, and so on. The MV detector imaging data acquired in steps (402-406) may be stored in a processor memory of a radiotherapy system and/or treatment planning system. Segmenting (408) a treatment plan fluence map may be similar to the segmentation method described above in FIG. 2 (e.g., step 208).

Some variations of method (400) may comprise determining (409) one or more sets of single-leaf opening imaging data and fill-in profiles that create the pattern of MLC openings. For example, method (400) may comprise determining a first set of single-leaf openings and a second set of fill-in profiles that may be summed together. The first and second sets may include all of the single-leaf openings and fill-in profiles for all of the MLC configurations that comprise the segmented fluence map for the entire treatment. For example, the first and second sets may include all of the single-leaf openings and fill-in profiles for the MLC configurations at each firing position for multiple gantry rotations (in the case of a radiotherapy system with a rotatable gantry), for multiple beam stations (i.e., multiple discrete patient platform positions at which the platform is stopped while radiation is delivered), and/or for multiple shuttle passes through the treatment beam (i.e., moving the patient platform through the treatment beam multiple times, where each instance through the treatment beam is one pass). Alternatively, or additionally, determining (409) one or more sets of single-leaf openings and fill-in profiles may comprise generating a set of single-leaf openings and a set of fill-in profiles for each shuttle pass. An expected MV detector image may be generated for each shuttle pass, and during treatment delivery QA, the quality of the radiation delivery may be evaluated on a pass-by-pass basis.

In some variations, method (400) may comprise placing (401) one or more phantoms and/or fluence measurement devices within a field of view of an MV detector before acquiring (402, 404) MV detector imaging data of single-leaf and double-leaf openings. The phantom(s) may comprise regions that have radiation attenuation and/or absorption properties that mimic those of patient tissue and/or tumor tissue. These MV detector imaging data of single-leaf and double-leaf openings in the presence of a phantom may be used in the same manner as the imaging data of single-leaf and double-leaf openings in the absence of a phantom. The MV detector data in the presence of a phantom may be used to generate an expected MV detector image when a treatment plan fluence map is delivered to a phantom (which may mimic or model the anatomical and/or physiological aspects of a patient and/or tumors). Alternatively, or additionally, the phantom(s) may comprise a fluence measurement device. Examples of fluence measurement devices may include, but are not limited to, a diode array, thin film transistor (TLT), thermoluminescent dosimeter (TLD), film, and/or any radiation photon detection device. The measurements acquired by the fluence measurement device(s) acquired during a radiation delivery QA session may be compared with the MV detector imaging data, and the comparison may be used to calculate a calibration factor that relates the MV detector imaging data to the measurements from the fluence measurement device(s). The calibration factor may be used to perform an absolute dose calculation during a radiation delivery session, e.g., a treatment session. In some variations, methods may comprise calculating a radiation dose to the phantom using the generated radiation detector image based on the acquired MV detector data and the known geometric and material properties of the phantom. After the dose delivered to the phantom is determined, the delivered dose may be evaluated using metrics such as gamma evaluation (e.g., gamma index analysis). For example, the gamma index value for various points on the test dose distribution (the delivered dose distribution to the phantom) and reference dose distribution (the expected or planned dose distribution, i.e., dose according to the treatment plan) may be calculated and compared to a passing gamma index threshold to determine whether the dose difference is acceptable. In some variations, a gamma evaluation may include determining whether the delivered dose distribution meets dose-difference (DD) and/or distance-to-agreement (DTA) criteria (e.g., 3%/3 mm) for multiple points on the distribution.

After an MV detector image is generated using the single-leaf, double-leaf, and/or fill-in profile imaging data according to any of the methods described herein (e.g., the methods described and depicted in FIGS. 2-4), a graphical representation that includes the generated MV detector image may be generated and output to a display device. The generated MV detector image may be compared to an acquired MV detector image to evaluate whether a radiotherapy system precisely delivered radiation according to a treatment plan fluence map.

Figure 6:
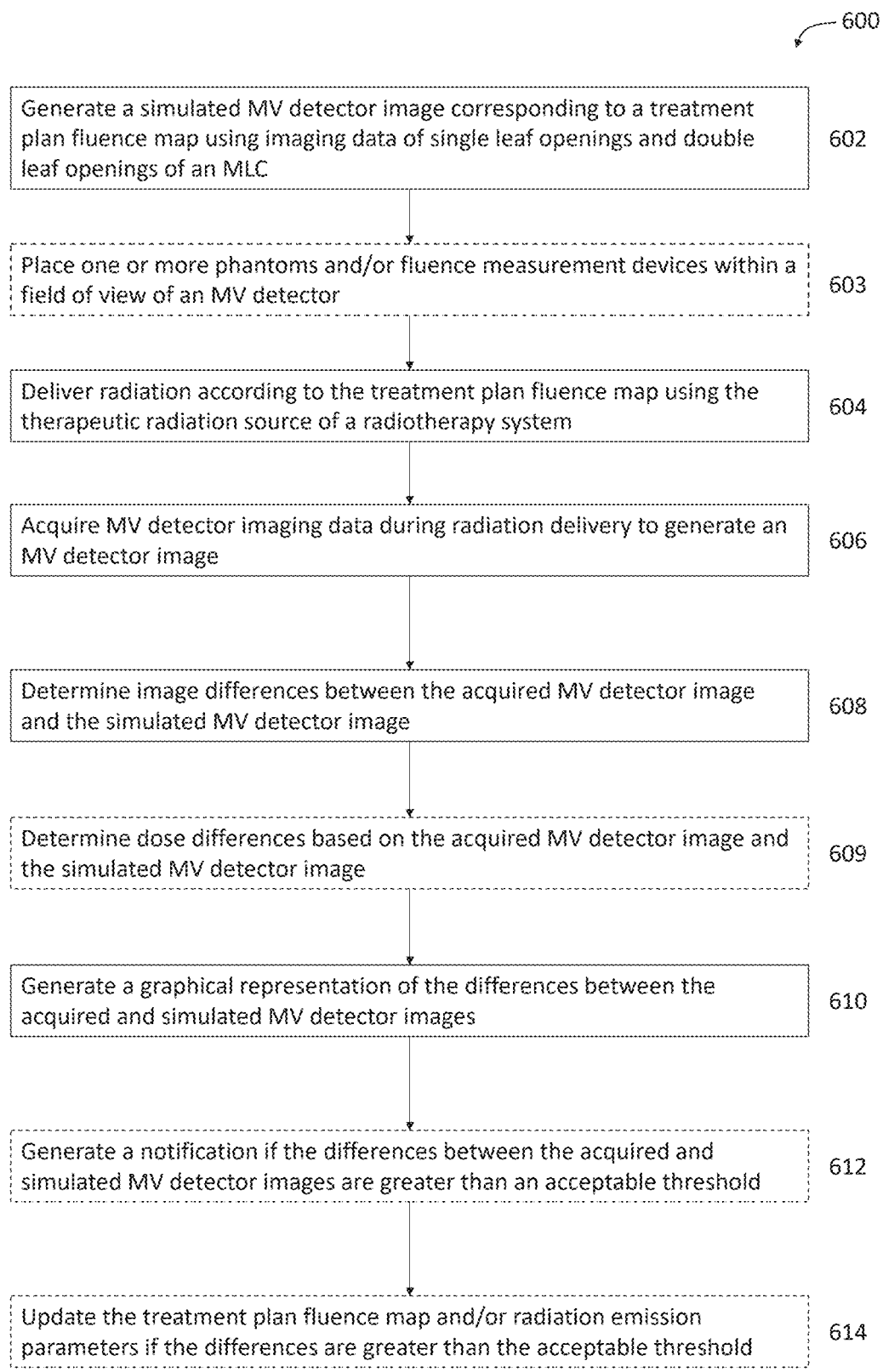
FIG. 6 is a flowchart representation of one variation of a method for evaluating the quality of radiation delivery according to a patient-specific treatment plan.

One variation of a method for evaluating the quality of radiation delivery is depicted in FIG. 6. Method (600) may comprise generating (602) a simulated MV detector image corresponding to a treatment plan fluence map using imaging data of single leaf openings and double leaf openings of an MLC (e.g., using methods (200) or (400)), delivering (604) radiation according to the treatment plan fluence map using the therapeutic radiation source of a radiotherapy system, acquiring (606) MV detector imaging data during radiation delivery to generate an MV detector image, determining (608) image differences between the acquired MV detector image and the simulated MV detector image, and generating (610) a graphical representation of the differences between the acquired and simulated MV detector images. The simulated MV detector image may be used as an expected MV detector image against which a test or QA MV detector image may be compared to determine whether the radiotherapy system is functioning properly and precisely enough to deliver a treatment plan radiation fluence map. The simulated MV detector image may be generated using the radiotherapy system controller, and/or a separate controller (e.g., a controller of a treatment planning or treatment QA system). Alternatively, or additionally, a radiotherapy system may comprise one or more controllers, at least one of which may be configured to generate a simulated MV detector image. In some variations, if the differences between the acquired and the simulated/expected MV detector images (and/or the delivered and expected dose distributions, described further below) are greater than a predetermined acceptable threshold, method (600) may further comprise generating (612) a notification. The notification may be incorporated into the graphical representation and output to a display device, and/or may be an audible notification. In some variations, the graphical representation may also include a visual indication that the differences between the acquired and simulated/expected MV detector images are within an acceptable range (e.g., below the difference threshold) and therefore, the radiation delivery has "passed" the QA session. If the differences are greater than the acceptable threshold, method (600) may comprise updating (614) the treatment plan fluence map and/or radiation emission parameters. For example, if the delivered radiation as indicated in the acquired MV detector images seems to differ from the expected MV detector images around the edges, the performance of the MLC leaves on either end of the MLC (e.g., leaves 1 to 10 and leaves 54-64) may be evaluated. If the end-leaves are not performing with sufficient precision, the treatment plan fluence map may be re-segmented such that other MLC leaves (e.g., central-MLC leaves) are used with a greater frequency than the end leaves. Alternatively, the system may be checked to make sure that all of the leaves are operating according to pre-defined specifications.

Alternatively, or additionally, the acquired MV detector image and the simulated/expected MV detector image may be used to generate corresponding dose distribution maps, i.e., a delivered dose distribution and an expected dose distribution. The delivered dose distribution may be generated based on the acquired MV detector image and the expected dose distribution may be generated based on the simulated MV detector image. For example, the expected dose distribution may be generated using a controller (e.g., radiotherapy system controller and/or treatment planning or QA controller) by loading the simulated MV detector image, loading the treatment plan fluence map (e.g., radiation beamlet sequence), and generating the expected dose distribution, Method (600) may comprise determining (609) dose differences between the delivered dose distribution and the expected dose distribution. The generated dose distributions may be overlaid with anatomical images of the patient and included with the graphical representation that is output to a display device. The delivered and expected dose distributions may help a clinician determine whether any radiation delivery parameters and/or treatment planning parameters should be adjusted. The delivered dose distribution may be evaluated using the expected dose distribution as the reference dose with metrics such as gamma evaluation (e.g., gamma index analysis). For example, the gamma index value for various points on the test dose distribution (the delivered dose distribution) and reference dose distribution (the expected dose distribution) may be calculated and compared to a passing gamma index threshold to determine whether the dose difference is acceptable. In some variations, a gamma evaluation may include determining whether the delivered dose distribution meets dose-difference (DD) and/or distance-to-agreement (DTA) criteria (e.g., 3%/3 mm) for multiple points on the distribution. The determined (609) dose differences may optionally be graphically and/or textually depicted on the generated (610) graphical representation.

Optionally, in some variations, method (600) may comprise placing (603) one or more phantoms and/or fluence measurement devices within a field of view of an MV detector before delivering (604) radiation. As described previously, the phantom(s) may have geometric and/or material properties that mimic those of a patient so that the acquired MV detector imaging data may better represent the radiation scatter and attenuation due to a patient during a treatment session. In this variation, the simulated or expected MV detector image used for comparison may be generated using the single-leaf and double-leaf MV detector imaging data acquired in the presence of a phantom (e.g., a similar or the same phantom). The fluence measurement device(s), which may be used alone or in combination with a phantom, may record measurements of the radiation received at the treatment area of the radiotherapy system, and these measurements may be calibrated with the acquired MV detector measurements. The resulting calibration factor may be used during a QA session and/or a treatment session for calculating the radiation dose delivered to the treatment area based on the MV detector measurements. In some variations, steps (603-606) may be performed on a radiotherapy system comprising a linac, MLC, MV detector and a radiotherapy system controller (e.g., the radiotherapy system described above), while steps (608-614) may be performed using the radiotherapy system controller and/or a separate controller (e.g., a controller of a treatment planning or treatment QA system). Alternatively, or additionally, a radiotherapy system may comprise one or more controllers, at least one of which may be in communication with the linac, MLC, and MV detector, and at least one of the other controllers may be configured to perform one or more of the steps in method (600). For example, a first radiotherapy system controller may be configured to perform steps (603-606) while a second radiotherapy system controller may be configured to perform steps (608-614).

While various inventive variations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments/variations described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive variations described herein. It is, therefore, to be understood that the foregoing variations are presented by way of example only and that, within the scope of the appended claims and equivalents thereto, inventive variations may be practiced otherwise than as specifically described and claimed. Inventive variations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A method for generating a radiation detector image that corresponds to a treatment plan fluence map multi-leaf opening pattern, the method comprising:
   acquiring imaging data of a single leaf opening using a radiation source and a radiation detector for each leaf of a multi-leaf collimator (MLC);
   acquiring imaging data of a double leaf opening using the radiation source and the radiation detector for each leaf of the MLC;
   segmenting a treatment plan fluence map into a pattern of MLC openings; and
   generating a radiation detector image that corresponds to the treatment plan fluence map by combining the acquired imaging data of single leaf and double leaf openings according to the pattern of MLC openings.

2. The method of claim 1, further comprising generating a graphical representation that comprises the generated radiation detector image and outputting the graphical representation to a display device.

3. The method of claim 1, further comprising calculating a radiation dose to a phantom based on the generated radiation detector image.

4. The method of claim 1, wherein the radiation detector is a MV detector.

5. The method of claim 1, wherein the radiation source and radiation detector are mounted on a gantry rotatable to multiple firing positions, and wherein acquiring imaging data of a single leaf opening and a double leaf opening comprises rotating the gantry to a first firing position and acquiring imaging data of a single leaf opening and a double leaf opening at the first firing position, and rotating the gantry to a second firing position and acquiring imaging data of a single leaf opening and a double leaf opening at the second firing position.

6. The method of claim 5, further comprising acquiring imaging data of single leaf openings and double leaf openings for each leaf of the MLC at the first firing position.

7. The method of claim 6, further comprising acquiring imaging data of single leaf openings and double leaf openings for each leaf of the MLC at the second firing position.

8. The method of claim 1, wherein the pattern of MLC openings comprises a plurality of MLC leaf instructions designating leaf positions for each MLC leaf.

9. The method of claim 1, wherein the pattern of MLC openings comprises a plurality of single leaf openings and a plurality of double leaf openings.

10. The method of claim 1, wherein combining the acquired imaging data comprises summing the acquired imaging data of single leaf openings and the acquired imaging data of double leaf openings, and subtracting the imaging data of single leaf openings from areas of overlap in summed imaging data of double leaf openings.

11. The method of claim 1, further comprising placing a phantom within a field of view of the radiation detector before acquiring radiation detector imaging data of single MLC leaf openings and double MLC leaf openings.

12. The method of claim 1, further comprising placing a radiation fluence measurement device within a field of view of the radiation detector before acquiring radiation detector imaging data of single MLC leaf openings and double MLC leaf openings.

13. The method of claim 1, wherein the acquired imaging data of single leaf openings, the acquired imaging data of double leaf openings, the pattern of MLC openings, and the generated radiation detector images are stored in a processor memory of a radiation delivery system.

14. The method of claim 1, further comprising calculating a fill-in profile for each pair of adjacent MLC leaves by subtracting the imaging data of the two single MLC leaf openings from the imaging data of the corresponding double MLC leaf opening and wherein generating a radiation detector image that corresponds to the treatment plan fluence map comprises combining the acquired imaging data of single leaf openings and fill-in profiles according to the pattern of MLC openings.

15. The method of claim 14, wherein combining the acquired imaging data of single leaf openings and the fill-in profiles comprises summing the acquired imaging data of single leaf openings and the fill-in profiles for adjacent single leaf openings.

16. The method of claim 14, wherein generating the radiation detector image further comprises combining acquired imaging data of double leaf openings with the imaging data of single leaf openings and fill-in profiles.

17. The method of claim 14, further comprising generating a graphical representation of the generated radiation detector image and outputting the graphical representation to a display device.

18. The method of claim 14, further comprising calculating a radiation dose to a phantom based on the generated radiation detector image.

19. The method of claim 14, wherein the radiation detector is an MV detector.

20. The method of claim 19, wherein the radiation source and radiation detector are mounted on a gantry rotatable to multiple firing positions, and wherein acquiring imaging data of a single leaf opening and a double leaf opening comprises rotating the gantry to a first firing position and acquiring imaging data of a single leaf opening and a double leaf opening at the first firing position, and rotating the gantry to a second firing position and acquiring imaging data of a single leaf opening and a double leaf opening at the second firing position.

21. The method of claim 20, further comprising acquiring imaging data of single leaf openings and double leaf openings for each leaf of the MLC at the first firing position.

22. The method of claim 21, further comprising acquiring imaging data of single leaf openings and double leaf openings for each leaf of the MLC at the second firing position.

23. The method of claim 14, wherein the pattern of MLC openings comprises a plurality of MLC leaf instructions designating leaf positions for each leaf of the MLC.

24. The method of claim 14, wherein the pattern of MLC openings comprises a plurality of single leaf openings and a plurality of double leaf openings.

25. The method of claim 14, further comprising placing a phantom within a field of view of the radiation detector before acquiring radiation detector imaging data of single MLC leaf openings and double MLC leaf openings.

26. The method of claim 14, further comprising placing a radiation fluence measurement device within a field of view of the radiation detector before acquiring radiation detector imaging data of single MLC leaf openings and double MLC leaf openings.

27. The method of claim 14, wherein the acquired imaging data of single leaf openings, the acquired imaging data of double leaf openings, the pattern of MLC openings, and the generated radiation detector images are stored in a processor memory of a radiation delivery system.

28. A radiotherapy system comprising a radiation source, a multi-leaf collimator (MLC), a radiation detector and one or more controllers, at least one of which is in communication with each of the radiation source, MLC and imaging system, wherein the controller is, or the controllers are between them, configured to perform the steps of:
  acquiring imaging data of a single leaf opening using the radiation source and the radiation detector for each leaf of a multi-leaf collimator (MLC);
  acquiring imaging data of a double leaf opening using the radiation source and the radiation detector for each leaf of the MLC;
  segmenting a treatment plan fluence map into a pattern of MLC openings; and
  generating a radiation detector image that corresponds to the treatment plan fluence map by combining the acquired imaging data of single leaf and double leaf openings according to the pattern of MLC openings.

29. The system of claim 28, wherein the system further comprises a display device and the controller is further configured to generate a graphical representation that comprises the generated radiation detector image and output the graphical representation to the display device.

30. The system of claim 28, wherein the one or more controllers is further configured to calculate a radiation dose to a phantom based on the generated radiation detector image.

31. The system of claim 28, wherein the radiation detector is a MV detector.

32. The system of claim 28, wherein the radiation source and radiation detector are mounted on a gantry rotatable to multiple firing positions, a first of the one or more controllers being configured to acquire imaging data of a single leaf opening and a double leaf opening by rotating the gantry to a first firing position and using the radiation source and the radiation detector to acquire imaging data of a single leaf opening and a double leaf opening at the first firing position, rotating the gantry to a second firing position and using the radiation source and the radiation detector to acquire imaging data of a single leaf opening and a double leaf opening at the second firing position.

33. The system of claim 32, wherein the first controller is further configured to acquire imaging data of single leaf openings and double leaf openings for each leaf of the MLC at the first firing position.

34. The system of claim 33, wherein the first controller is further configured to acquire imaging data of single leaf openings and double leaf openings for each leaf of the MLC at the second firing position.

35. The system of claim 28, wherein the pattern of MLC openings comprises a plurality of MLC leaf instructions designating leaf positions for each MLC leaf.

36. The system of claim 28, wherein the pattern of MLC openings comprises a plurality of single leaf openings and a plurality of double leaf openings.

37. The system of claim 28, wherein combining the acquired imaging data comprises summing the acquired imaging data of single leaf openings and the acquired imaging data of double leaf openings, and subtracting the imaging data of single leaf openings from areas of overlap in summed imaging data of double leaf openings.

38. The system of claim 28, wherein the system further comprises a processor memory and the acquired imaging data of single leaf openings, the acquired imaging data of double leaf openings, the pattern of MLC openings, and the generated radiation detector images are stored in the processor memory.

39. The system of claim 28, wherein the one or more controllers is further configured to calculate a fill-in profile for each pair of adjacent MLC leaves by subtracting the imaging data of the two single MLC leaf openings from the imaging data of the corresponding double MLC leaf opening and wherein generating the radiation detector image that corresponds to the treatment plan fluence map comprises combining the acquired imaging data of single leaf openings and fill-in profiles according to the pattern of MLC openings.

40. The system of claim 39, wherein combining the acquired imaging data of single leaf openings and the fill-in profiles comprises summing the acquired imaging data of single leaf openings and the fill-in profiles for adjacent single leaf openings.

41. The system of claim 39, wherein generating the radiation detector image further comprises combining acquired imaging data of double leaf openings with the imaging data of single leaf openings and fill-in profiles.

42. The system of claim 39, wherein the system further comprises a display device and the controller is further configured to generate a graphical representation of the generated radiation detector image and output the graphical representation to the display device.

43. The system of claim 39, wherein a second of the one or more controllers is further configured to calculate a radiation dose to a phantom based on the generated radiation detector image.

44. The system of claim 39, wherein the radiation detector is an MV detector.

45. The system of claim 28, wherein the radiation source and radiation detector are mounted on a gantry rotatable to multiple firing positions, the one or more controllers being configured to acquire imaging data of a single leaf opening and a double leaf opening by rotating the gantry to a first firing position and acquiring imaging data of a single leaf opening and a double leaf opening at the first firing position, and rotating the gantry to a second firing position and acquiring imaging data of a single leaf opening and a double leaf opening at the second firing position.

46. The system of claim 45, wherein the one or more controllers is further configured to acquire imaging data of single leaf openings and double leaf openings for each leaf of the MLC at the first firing position.

47. The system of claim 46, wherein the one or more controllers is further configured to acquire imaging data of single leaf openings and double leaf openings for each leaf of the MLC at the second firing position.

48. The system of claim 39, wherein the pattern of MLC openings comprises a plurality of MLC leaf instructions designating leaf positions for each leaf of the MLC.

49. The system of claim 39, wherein the pattern of MLC openings comprises a plurality of single leaf openings and a plurality of double leaf openings.

50. The system of claim 39, wherein the one or more controllers comprises a processor memory and the acquired imaging data of single leaf openings, the acquired imaging data of double leaf openings, the pattern of MLC openings, and the generated radiation detector images are stored in the processor memory.

51. The system of claim 28, wherein the one or more controllers comprise a first controller that is in communication with each of the radiation source, MLC and imaging system and a second controller, and a second controller, wherein the first controller is configured to perform the steps of acquiring imaging data of a single leaf opening using the radiation source and the radiation detector for each leaf of the MLC and acquiring imaging data of a double leaf opening using the radiation source and the radiation detector for each leaf of the MLC, and wherein the second controller is configured to perform the steps of segmenting a treatment plan fluence map into a pattern of MLC openings and generating a radiation detector image that corresponds to the treatment plan fluence map by combining the acquired imaging data of single leaf and double leaf openings according to the pattern of MLC openings.

\* \* \* \* \*